United States Patent [19]

Fenton et al.

[11] Patent Number: 4,918,210
[45] Date of Patent: Apr. 17, 1990

[54] ZWITTERIONIC POLYSILOXANE COMPOSITIONS

[76] Inventors: William N. Fenton, 3831 N. Jefferson; Michael J. Owen, 2808 Lambros Dr.; Steven A. Snow, 1511 Sylvan La., all of Midland, Mich. 48640

[21] Appl. No.: 4,734

[22] Filed: Jan. 20, 1987

[51] Int. Cl.$^4$ .............................. C07F 7/08; C07F 7/10
[52] U.S. Cl. .................................... 556/425; 556/413; 252/309; 252/312; 252/357
[58] Field of Search ................. 556/425; 252/312, 309, 252/357

[56] References Cited

U.S. PATENT DOCUMENTS

| | | | |
|---|---|---|---|
| 3,624,120 | 11/1971 | Yetter | 556/425 |
| 3,836,559 | 9/1974 | Prokai | 556/425 |
| 4,093,642 | 6/1978 | Schilling et al. | 556/425 X |
| 4,496,705 | 1/1985 | Florence et al. | 556/413 X |
| 4,525,567 | 6/1985 | Campbell et al. | 556/425 X |

Primary Examiner—Paul F. Shaver

[57] ABSTRACT

A zwitterionic composition useful as a surface active agent in aqueous solutions. Said composition represented by the general formula $$R'(CH_3)_2Si-O[SiO(CH_3)_2]_w[SiCH_3R-O]_x-Si(CH_3)_2R'$$

where w is 0, to 50, x is 1, 2, 3, 4 or 5, R' denotes a methyl radical or an R radical, x + w is less than or equal to 50 and R denoted a monovalent zwitterionic radical of the general formula $$-(CH_2)_yN^+(R'')_2(CH_2)_zSO_3^-$$

where y is 1, 2 or 3, z is 3 or 4, and R'' denotes an alkyl radical with 1 to 6 carbon atoms.

20 Claims, No Drawings

ZWITTERIONIC POLYSILOXANE COMPOSITIONS

BACKGROUND OF THE INVENTION

The present invention relates to polysiloxane based zwitterionic surfactants. Polysiloxane based surfactants have heretofore been either anionic, cationic, amphoteric or nonionic species. Such surfactants are useful as polyurethane foam additives, as mold release coatings, and in a variety of other applications. In general, polysiloxane based surfactants are more effective and efficient than their organic counterparts. For instance, polysiloxane based commercial surfactants reduce the surface tension of aqueous systems to about 20-25 dynes/centimeter whereas organic surfactants reduce the surface tension of such systems to about 30-35 dynes/centimeter. Furthermore, polysiloxane based surfactants achieve their optimal results with about one tenth to one one-hundredth the concentration with which organic surfactants achieve their optimal results.

Organic zwitterionic surfactants are known in the art to be compatible with a wide range of surfactants which allows them to be more readily formulated, and they are also known to be less irritating to eyes and skin than other types of surfactants. Thus, organic zwitterionic surfactants such as quaternized imidazoline derivatives are used in shampoos and soaps.

Zwitterionic organofunctional silicones are also known in the art, although to a much lesser extent than zwitterionic organic surfactants. DE 3,417,912 issued to Kollmeier, et al. and assigned to Th. Goldschmidt AG teaches betaine functional short polysiloxane chain materials of the general formula

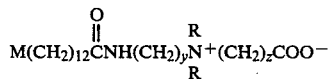

where M is a polysiloxane polymer; y is 2 to 4, z is 1 to 3, and R denotes an alkyl radical with 1 to 4 carbon atoms. UK patent application GB 2,161,172A, applied for by the Beecham Group, teaches the use of polysiloxane polyorganobetaine copolymers in shampoo formulations. Neither patent teaches the use of zwitterionic organofunctional polysiloxanes as a surfactant for lowering the surface tension of aqueous solutions. U.S. Pat. No. 4,496,705, issued to Florence et al. and assigned to the General Electric Corporation, teaches zwitterionic organofunctional polysiloxanes where the polysiloxane backbone of the finished product has a degree of polymerization of about 800. Florence teaches that these materials are elastomers which show improved adhesion to glass over state of the art elastomers. Florence et al. does not teach that these materials are surface active agents particularly effective in lowering the surface tension of aqueous solutions.

Graiver et al. teach organofunctional polysiloxanes of the general formula

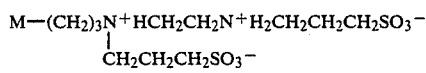

where M is a polysiloxane polymer. These materials are zwitterionic at certain pH values. See "Polysiloxane Zwitterionomers and Related Model Compounds", Parts I-III, Journal of Polymer Science, Polymer Chemistry Edition. V.17 p3559-3605 (1979). Graiver et al. do not teach that their materials, which differ from the claimed compositions of the present application in that they are not alkyl quaternary ammonium salts, are effective surface active agents which can lower the surface tension of aqueous solutions.

SUMMARY OF THE INVENTION

The present invention relates to novel zwitterionic polysiloxane compositions represented by the general formula

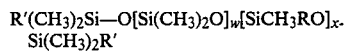

where w is 0 to about 50, x is 0, 1, 2, 3, 4, or 5 and the sum of w+x is less than or equal to 50. When the sum of x+w is greater than 20, then the mole percent of R radical containing siloxane units should be less than about 5 mole %. Materials with x+w average sums less than or equal to about 20 are preferred surfactants. The most preferred surfactants are those materials with x+w average sums less than about 10. The most preferred embodiments have w equal to 1, 2, or 3 and x equal to 0, 1, or 2 on the average. In any event the molecule must have at least one R radical. R' denotes a methyl radical or an R radical, and R denotes a monovalent zwitterionic radical of the general formula

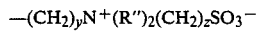

where y is 1, 2, or 3, z is 3 or 4 and R" denotes an alkyl radical with 1 to 6 carbon atoms. These novel surfactant compositions effectively and efficiently lower the surface tension of aqueous solutions, remain zwitterionic over a wide pH range, and are superior to organic zwitterionic surfactants in many applications.

DETAILED DESCRIPTION OF THE INVENTION

This invention relates to novel zwitterionic polysiloxane compositions represented by the general formula

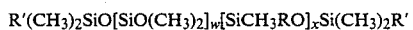

where w is 0 to about 50, x is 0, 1, 2, 3, 4, or 5 and the sum of w and x is less than or equal to about 50. When the sum of x+w is greater than 20 then the mole percent of R radical containing siloxane units should be less than about 5 mole %. Materials with x+w average sums less than or equal to about 20 are preferred surfactants. The most preferred surfactants are those materials with x+w average sums less than about 10. The most preferred embodiments have w equal to 0, 1, 2, or 3 and x equal to 1, or 2 on the average. In any event the molecule has at least one R radical. R' denotes a methyl radical or an R radical, and R denotes a monovalent zwitterionic radical of the general formula

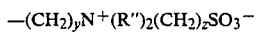

where y is 1, 2, or 3, z is 3 or 4, and R" denotes an alkyl radical with 1 to 5 carbon atoms. These materials are particularly efficient and effective aqueous surfactants and display surprising dynamic surface tension reducing properties in aqueous solutions. For the purposes of the present invention these materials will be called "sulfobetaine" functional polysiloxanes.

Specific examples of compounds within the scope of the invention include, but are not limited to, compounds of the following formulae:

$R(CH_3)_2SiOSi(CH_3)_2R$, (A)

$(CH_3)_3SiOSi(CH_3)_2R$, (B)

$(CH_3)_3SiO—SiCH_3ROSi(CH_3)_3$, (C)

$(CH_3)_3SiO—[SiCH_3RO]_2—Si(CH_3)_3$, (D)

$(CH_3)_3Si—OSi(CH_3)_2O—SiCH_3RO—Si(CH_3)_3$, (E)

$(CH_3)_3Si—OSi(CH_3)_2O]—[SiCH_3RO]_2Si(CH_3)_3$, (F)

$(CH_3)_3Si—O[Si(CH_3)_2O]_2—SiCH_3ROSi(CH_3)_3$, and (G)

$(CH_3)_3Si—O[Si(CH_3)_2O]_3—SiCH_3ROSi(CH_3)_3$ (H)

where R represents a monovalent zwitterionic radical chosen from radicals which include, but are not limited to $—(CH_2)_3N^+(R'')_2(CH_2)_3SO_3^-$, and $—(CH_2)_3N^+(R'')_2(CH_2)_4SO_3^-$ These compounds are synthesized by a two step process comprising: 1. a hydrosilation reaction which involves reacting a Si-H functional precursor with N-allyl-N,N-dimethylamine, or other functionally similar chemicals, in the presence of platinum metal catalyst to form a tertiary amine functional siloxane compound; and, 2. a sulfopropylation or sulfobutylation reaction which involves reacting the product of step 1 with either cyclic 1,3-propanesultone or cyclic 1,4-butanesultone, or other similar chemicals.

The Si-H functional precursors can be prepared by a number of different methods known in the art. For instance, the precursor can be prepared by equilibrating a commercially available long chain Si-H functional polysiloxane, cyclic polydimethylsiloxanes, and hexamethyldisiloxane in the presence of an acid catalyst. The particular precursor prepared will be a function of the proportion of starting materials. Particularly pure precursors can be prepared by the same method with careful distillation of the reaction product. Many of the polysiloxane precursors used to make compounds within the scope of the invention are commercially available.

The amine functional compound reacted with the Si-H functional precursor must have a tertiary amine functional radical in an allylic position. The tertiary amine functional compounds which are useful in the preparation of the present invention include N-allyl-N,N-dimethylamine and N-allyl-N,N-diethylamine. These tertiary amines are commercially available.

Typically the first step in the synthesis, the hydrosilation reaction, is run solventlessly at between 90° and 110° C. with between 1 and 100 ppm platinum metal catalyst. The reaction is usually complete between 90 minutes and 2 hours, and the reaction product can be purified by distillation. The resulting tertiary amine functional polysiloxane can be produced with greater than 80 weight percent purity.

The second step of the reaction is run at between about 50° C. and 150° C. in a mutual solvent of the cyclic alkylsultone and the tertiary amine functional polysiloxane for about 2 hours. The resulting reaction mixture can be purified by first removing the reaction solvent and then filter rinsing with toluene, alcohols, or ethers.

The final products of the above syntheses can be used as surface active agents for aqueous solutions. These surface active agents are both effective and efficient surface active agents. The effectiveness of a surfactant is measured by the extent that a surfactant lowers the surface tension of a solution independent of the concentration of surfactant used. The compounds of the present invention are effective in that they lower the surface tension of aqueous systems from greater than 50 dynes/centimeter to less than 25 dynes/centimeter. They are efficient in that they decrease the surface tension of aqueous systems at much lower surfactant concentrations than organic surfactants require to achieve the same results. In fact, the compounds of the present invention are both more effective and efficient than organic zwitterionic surfactants. The compounds of the present invention achieve significant surface tension decreases with as little as 0.5 weight percent concentration. Some embodiments of the present invention achieve full surface tension reduction at as little as 0.005 weight percent concentration.

These silicone sulfobetaines are also very effective and efficient surfactants in the dynamic reduction of aqueous surface tension. In particular, the species where $w=0$, $x=1$ are excellent surfactants in this regard. Dynamic aqueous surface tension was measured using the maximum bubble pressure technique, where the bubbles were introduced into the surfactant solutions at variable rates and the surface tension at the bubble/water interface was continuously monitored. Dynamic reduction of the aqueous surface tension to 30 dyne/centimeter at bubble rates of 3–5 per second were observed.

The compositions of the present invention can be used to stabilize oil in water and water in oil emulsions. The compositions of the present invention are thought to be particularly effective in stabilizing emulsions where the oil is a polysiloxane. Such polysiloxanes include cyclic compounds of the formula

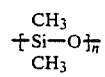

where n is 3, 4, 5, 6, 7, or 8 and combination thereof, and linear polydiorganosiloxanes of the general formula

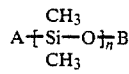

where n is on the average between 10 and 5000, A denotes a trimethoxysiloxy or trimethylsiloxy radical and B denotes a trimethoxysilyl or trimethysilyl radical. Such emulsions are useful in deodorant, antiperspirant, skin care and other cosmetic formulations.

EXAMPLES

The following examples illustrate the synthesis of the compositions of the present invention. The examples also demonstrate the efficiency and effectiveness of these compositions as surface active agents for aqueous systems.

EXAMPLE 1

Part 1

General Procedure for Synthesizing Si-H Functional Polysiloxanes

A sufficient amount of a polysiloxane of the average formula $$(CH_3)_3SiO[\underset{H}{\underset{|}{Si}}-O-]_{40}Si(CH_3)_3 \quad (A)$$

was placed in a three neck round bottom flask with a sufficient amount of cyclopolysiloxane of the general formula $$+\underset{CH_3}{\underset{|}{\overset{CH_3}{\overset{|}{Si}}}}-O+_n \quad (B)$$

where n is 4, 5 or 6, a sufficient amount of endblocker of the general formulae $$(CH_3)_3Si-O\underset{CH_3}{\underset{|}{\overset{CH_3}{\overset{|}{Si}}}}-O-Si(CH_3)_3, \text{ or} \quad (C)$$

$$(CH_3)_3Si-O-Si(CH_3)_3 \quad (D)$$

and an effective amount of acid catalyst to form the desired Si-H functional precursor. The reactants were equilibrated at about 65° C. for about 15 hours. The reacted mixture was filtered under nitrogen and analyzed by gas chromatography. The desired Si-H precursors could be highly purified by distillation in some cases. All of the various Si-H functional polysiloxanes produced by this general scheme were 80 to 98 wt % pure. The following table summarizes the precursors made. In the table M denotes a trimethylsiloxane endblocker unit, D denotes a dimethylsiloxane unit, and D' denotes a SiH functional monomethylsiloxane unit.

TABLE 1

| | | Precursor Polysiloxanes | | | | | |
|---|---|---|---|---|---|---|---|
| | | % | Formulation WT | | | | Distillation |
| Structure | MW | SiH | A | B | C | D | mm Hg/C |
| MD'D'M | 282 | 0.70 | 45.3 | — | — | 54.7 | <5 @ 69 |
| MDD'M | 296 | 0.34 | 21.6 | 0.5 | 77.8 | — | <2 @ 49 |
| MDD'D'M | 356 | 0.56 | 35.7 | 1.2 | 63.1 | — | <4 @ 79 |
| MDDD'M | 370 | 0.27 | 17.2 | 20.5 | 62.3 | — | <2 @ 69 |
| MDDDD'M | 444 | 0.23 | 14.6 | 33.4 | 51.9 | — | <2 @ 91 |

SiH functional siloxanes of the general formula MM' and MD'M were commercially available and were so acquired.

Part 2

Synthesizing Tertiary Amine Functional Polysiloxanes

N-allyl-N,N-dimethylamine was reacted with the SiH functional polysiloxane precursors by combining 1:1 mole portions of the amine with each SiH functionality. The two reactants were mixed, and between 25 and 35 ppm Pt metal as chloroplatinic acid was added to the mixture. The catalyzed mixtures were reacted at 110° to 145° C. for about 90 minutes. The samples were distilled to give between 85 and 98 wt % purity as measured by gas chromatography. The following table summarizes the compounds made according to this general procedure.

TABLE 2

| | Allyldimethylamine Compound Summary | | | |
|---|---|---|---|---|
| | | Formulation Wt | | |
| Siloxane | MW | Siloxane | Amine | GC Purity |
| MD'M | 307 | 72.3 | 27.7 | >98% |
| MD'D'M | 367 | — | — | — |
| MDD'M | 381 | 79.7 | 20.3 | — |
| MDD'D'M | 441 | — | — | — |
| MDDD'M | 455 | 74.6 | 25.4 | 85% |
| MDDDD'M | 529 | 74.6 | 25.4 | 88% |

In table 2, M denotes $(CH_3)_3SiO_{\frac{1}{2}}-$, D denotes $-Si(CH_3)_2-O-$, and D' denotes $-Si(CH_3)(CH_2CH_2CH_2N(CH_3)_2)-O-$.

N-allyl-N,N-diethylamine was reacted with a polysiloxane precursor of the formula $$(CH_3)_3Si-O-\underset{H}{\underset{|}{\overset{CH_3}{\overset{|}{Si}}}}-O-Si(CH_3)_3$$

under the same conditions as above. The final distilled product, with a molecular weight of 345, was obtained in about 98 weight percent purity.

Part 3

Synthesizing the Zwitterionic "Sulfobetaine" Compounds

Equal molar parts cyclic propanesultone and tertiary amine functionality of the products of part 2 were reacted in various solvents for about two hours or until the reaction mixture solidified. The solvent was removed from the reaction product and the product was purified via solvent extraction of impurities. The following table summarizes the compounds made by this general method.

TABLE 3

| | | Surfactant Formulation Summary | | | | | | |
|---|---|---|---|---|---|---|---|---|
| | | | Formulation wt | | | | | |
| Compound | Product Formula | MW of Product | % Intermediate | % Propane Sultone | Solvent Medium | Rxn Temp | % Solids | Load Size, Grams |
| A | MM-R | 355 | 65.6 | 34.4 | Toluene | 96 | 70 | 21.6 |
| B | M(D-R)M | 429 | 71.8 | 28.2 | MeOH | 50 | 86 | 150.0 |
| C | MD(D-R)M | 503 | 75.7 | 24.3 | Toluene | 111 | 70 | 20.3 |
| D | M(D-R)$_2$M | 574 | 64.9 | 35.1 | MeOH | 60 | 70 | 91.8 |
| E | M(D)$_2$(D-R)M | 577 | 78.9 | 21.1 | Toluene | 113 | 70 | 16.6 |
| F | M(D)$_3$(D-R)M | 651 | 81.3 | 18.7 | Toluene | 113 | 70 | 13.3 |

TABLE 3-continued

Surfactant Formulation Summary

| Compound | Product Formula | MW of Product | Formulation wt % Intermediate | Formulation wt % Propane Sultone | Solvent Medium | Rxn Temp | % Solids | Load Size, Grams |
|---|---|---|---|---|---|---|---|---|
| G | MD(D-R)$_2$M | 770 | 68.3 | 31.7 | Toluene | 84 | 70 | 11.2 |

M denotes $(CH_3)_3SiO_{\frac{1}{2}}-$, D denotes a $-Si(CH_3)_2-O-$, and D-R and M-R are D and M radicals with an R group substituted for a methyl radical. R denotes the radical $$-CH_2CH_2CH_2N^+(CH_3)_2CH_2CH_2CH_2SO_3^-.$$

The compound represented by the formula M(D-R)M (hereinafter referred to as compound H) was also synthesized where M and D are defined as above and R denotes a radical of the formula $$-CH_2CH_2CH_2N^+(CH_2CH_3)_2CH_2CH_2CH_2SO_3^-$$

The structure of all compounds was confirmed by infrared spectroscopy, $^1$H NMR and $^{29}$Si NMR spectroscopies. Elemental analyses of the compounds was consistent with the proposed structures. The results of the analyses are reported in the following table.

Elemental Analysis Of Sulfobetaines

| Compound | Calculated C | Calculated H | Calculated N | Found C | Found H | Found N |
|---|---|---|---|---|---|---|
| B | 41.9 | 9.1 | 3.3 | 41.2 | 9.2 | 3.4 |
| C | 40.7 | 8.6 | 2.8 | 39.0 | 8.8 | 3.3 |
| D | 41.3 | 8.6 | 4.0 | 38.3 | 8.5 | 3.8 |
| E | 39.7 | 8.5 | 2.4 | 39.0 | 9.4 | 2.5 |
| F | 38.8 | 8.5 | 2.2 | 39.0 | 10.2 | 2.4 |
| G | 42.1 | 8.9 | 3.8 | 36.2 | 8.1 | 3.4 |
| H | 44.6 | 9.4 | 3.1 | 42.9 | 10.1 | 3.3 |

Surface Activity Studies

I. Equilibrium Surfactant Effectiveness and Efficiency

Each of the compounds synthesized in Example 1, Part 3 were dissolved in distilled water and the equilibrium surface tension of the resulting solutions was measured by the Wilhemy plate method at 25° C. at various surfactant concentrations. All compounds except D and G had the same surface tension effectiveness to 0.5 weight percent lowering the surface tension to about 21 dyne/cm. The results of the equilibrium study are summarized in Table 1. The results demonstrate compounds A, B, C, E, F, and G lower the equilibrium surface tension below 21 dyne/centimeter. In general, the compounds with more highly polymerized polysiloxane backbones were the most efficient surfactants.

TABLE 1

| Surfactant | Equilibrium Aqueous Surface Tension (dyne/cm) at Room Temperature at 0.01 wt. % | at 0.1 wt. % | at 1.0 wt. % | CMC |
|---|---|---|---|---|
| A | 41.0 | 28.5 | 21.0 | 0.29 |
| B | 39.3 | 25.6 | 21.0 | 0.31 |
| C | 26.5 | 21.0 | 21.0 | 0.03 |
| D | 25.2 | 23.4 | 22.5 | — |
| E | 23.5 | 21.0 | 21.0 | 0.01 |
| F | 22.0 | 21.0 | 21.0 | 0.005 |

TABLE 1-continued

| Surfactant | Equilibrium Aqueous Surface Tension (dyne/cm) at Room Temperature at 0.01 wt. % | at 0.1 wt. % | at 1.0 wt. % | CMC |
|---|---|---|---|---|
| H | 39.7 | 23.8 | 21.0 | 0.17 |

CMC is the critical micelle concentration, the wt% concentration at which the air/liquid interface is completely covered by the surfactant and micelle formation in solution begins.

Dynamic Surface Tension Studies

Equilibrium surface tension measurements are useful indications of a compound's effectiveness and efficiency as a surfactant; however, the end use of a surfactant often requires the material to migrate quickly through a solution in order to lower the surface tension at a liquid/air interface, or a liquid/liquid interface. Compounds, B, C, E, F, and H, were used to make 0.1 weight percent aqueous solutions. The dynamic surface tension of the solutions was tested by blowing bubbles in the solution to create fresh air/liquid interfaces and measuring the surface tension of the new interface by the maximum bubble pressure technique.

Compounds B, C, E, F and H displayed varied levels of effectiveness and efficiency as dynamic surface tension lowering agents. In general, the compounds with shorter polysiloxane backbones demonstrated better performance at increased bubble rates (the more dynamic systems).

However, what is clear from the test results is that the short polysiloxane chain compositions of the present invention are more effective in lowering the dynamic surface tension of aqueous solutions than commercially available hydrocarbon or fluorocarbon zwitteronic surfactants.

TABLE 2

| Surfactant Description | Dynamic Surface Tension Comparisons of 0.1 wt. % Active Surfactant Solutions Equilibrium Surface Tension | Dynamic Surface Tension 1 | 3 | 5 |
|---|---|---|---|---|
| Zonyl FSK ® | 18.4 | 33.3 | 44.7 | 50.4 |
| Armeen Z ® | 27.2 | 31.8 | 37.8 | 42.4 |
| Lonzaine C ® | 36.2 | 42.4 | 47.2 | 50.3 |
| B | 24.9 | 29.0 | 30.9 | 31.9 |
| H | 22 | 30 | 30 | 30 |
| C | 23 | 65 | 70 | 70 |
| E, F | 25 | 72 | 72 | 72 |

Zonyl FSK ® is a zwitterionic fluorocarbon surfactant sold by du Pont, Armeen Z ® is a zwitterionic organic surfactant sold by Akzo Chemie America, and Lonzaine C ® is a zwitterionic organic surfactant sold by the Lonza Corporation. All surface tensions are given in dyne/cm. Measurements were done at pH 7 at room temperature. The bubble rates are relative: 1 is the lowest bubble rate, 3 is an intermediate rate, and 5 is the rate which causes the surfactants to be least effective.

What is claimed is:

1. A composition represented by the general formula $$R'(CH_3)_2SiO[Si(CH_3)_2O]_w[SiCH_3RO]_xSi(CH_3)_2R'$$

where w is 0 to about 50, x is 0, 1, 2, 3, 4, or 5, the sum of x+w is less than or equal to about 50, R' denotes a methyl radical or an R radical, the molecule has at least one R radical, and R denotes a monovalent zwitterionic radical of the general formula $$-(CH_2)_yN^+(R'')_2(CH_2)_zSO_3^-$$

where y is 1, 2, or 3, z is 3 or 4 and R'' denotes an alkyl radical with 1 to 5 carbon atoms.

2. A composition represented by the general formula $$R'(CH_3)_2Si[Si(CH_3)_2O]_w[SiCH_3RO]_xSi(CH_3)_2R'$$

where w is 0, 1, 2, or 3, x is 0, 1 or 2, R' denotes a methyl radical or an R radical, and R denotes a monovalent zwitterionic radical of the general formula $$-(CH_2)_yN^+(R'')_2(CH_2)_zSO_3$$

where y is 1, 2, or 3, z is 3 or 4 and R'' denotes an alkyl radical with 1 to 5 carbon atoms.

3. The composition of claim 1 wherein x is 0, w is 0, and one R' denotes an R radical and the other R' denotes a methyl radical.

4. The composition of claim 1 wherein x is 0, w is 0 and both R's denote R radicals.

5. The composition of claim 1 wherein x is 1, w is 0, and R' denotes a methyl radical.

6. The composition of claim 1 wherein x is 1, w is 1, and R' denotes a methyl radical.

7. The composition of claim 1 wherein x is 2, w is 1, and R' denotes a methyl radical.

8. The composition of claim 1 wherein x is 2, w is 0, and R' denotes a methyl radical.

9. The composition of claim 1 wherein x is 1, w is 2, and R' denotes a methyl radical.

10. The composition of claim 1 wherein x is 1, w is 3, and R' denotes a methyl radical.

11. A composition comprising water and a sufficient amount of the composition of claim 1 to lower the surface tension of the resulting aqueous solution.

12. A composition comprising water and a sufficient amount of the composition of claim 2 to lower the surface tension of the resulting aqueous solution.

13. A composition comprising water and a sufficient amount of the composition of claim 3 to lower the surface tension of the resulting aqueous solution.

14. A composition comprising water and a sufficient amount of the composition of claim 4 to lower the surface tension of the resulting aqueous solution.

15. A composition comprising water and a sufficient amount of the composition of claim 5 to lower the surface tension of the resulting aqueous solution.

16. A composition comprising water and a sufficient amount of the composition of claim 6 to lower the surface tension of the resulting aqueous solution.

17. A composition comprising water and a sufficient amount of the composition of claim 7 to lower the surface tension of the resulting aqueous solution.

18. A composition comprising water and a sufficient amount of the composition of claim 8 to lower the surface tension of the resulting aqueous solution.

19. A method for lowering the surface tension of an aqueous solution which comprises adding a sufficient quantity of the composition of claim 1 to an aqueous solution to lower the surface tension of the resulting solution.

20. An emulsion comprising; an oil phase, an aqueous phase, and the composition of claim 1.

* * * * *